US008776576B2

(12) United States Patent  
Okada et al.

(10) Patent No.: US 8,776,576 B2  
(45) Date of Patent: Jul. 15, 2014

(54) GAS CHROMATOGRAPHY DEVICE

(71) Applicant: Shimadzu Corporation, Kyoto (JP)

(72) Inventors: Masayuki Okada, Kyoto (JP); Yasunori Terai, Osaka (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 13/717,659

(22) Filed: Dec. 17, 2012

(65) Prior Publication Data

US 2013/0219992 A1   Aug. 29, 2013

(30) Foreign Application Priority Data

Feb. 24, 2012 (JP) .................................. 2012-038635

(51) Int. Cl.
*G01N 30/02* (2006.01)
(52) U.S. Cl.
USPC ........................................ 73/23.41; 73/23.35
(58) Field of Classification Search
USPC ................... 73/23.41, 23.35, 23.4, 23.42
See application file for complete search history.

(56) References Cited

U.S. PATENT DOCUMENTS

| 2,400,923 A * | 5/1946 | Farr et al. ...................... 137/551 |
| 6,548,024 B1 * | 4/2003 | Doncaster et al. .............. 422/88 |
| 2010/0116021 A1 * | 5/2010 | O'Brien ........................ 73/23.37 |

FOREIGN PATENT DOCUMENTS

JP   H5-346424   12/1993

* cited by examiner

*Primary Examiner* — Daniel S Larkin  
*Assistant Examiner* — Jamar Ray  
(74) *Attorney, Agent, or Firm* — Jianq Chyun IP Office

(57) ABSTRACT

A gas chromatography device adapted for detecting leakage of hydrogen gas without using an air pump and long piping is provided. The gas chromatography device includes: a column oven having a housing, a column disposed in the housing, and a heater heating air in the housing; a sample vaporization chamber supplying a sample to an inlet end of the column; a carrier gas supply section supplying a carrier gas to the sample vaporization chamber; a detector connected to an outlet end of the column; a controller controlling the heater and the carrier gas supply section; and a hydrogen gas detecting sensor. The carrier gas is hydrogen gas. A through hole is formed in the housing and a material that allows hydrogen to pass through but does not transmit heat is disposed in the through hole. The hydrogen gas detecting sensor is disposed near the through hole outside the housing.

5 Claims, 4 Drawing Sheets

GAS CHROMATOGRAPHY DEVICE

CROSS-REFERENCE TO RELATED APPLICATION

This application claims the priority benefit of Japan application serial no. 2012-038635, filed on Feb. 24, 2012. The entirety of the above-mentioned patent application is hereby incorporated by reference herein and made a part of this specification.

BACKGROUND OF THE INVENTION

1. Field of the Invention

The invention relates to a gas chromatography device and particularly relates to a gas chromatography device utilizing hydrogen gas that serves as a carrier gas supplied to a column and a make-up gas flowing to a detector.

2. Description of Related Art

In a gas chromatography device, a sample gas is compressed and combined with a carrier gas and introduced into a column via an inlet end of the column. The substances contained in the sample gas, which are to be measured, are separated sequentially along a timeline when passing through the column and then reach an outlet end of the column. At the same time, a column oven, which includes the column therein, is used to adjust the temperature of the column, such that the sample gas passing through the column is maintained at a predetermined temperature. FIG. 5 is a structural diagram illustrating an example of the conventional gas chromatography device. A gas chromatography device 101 includes a column oven 2, a sample vaporization chamber 70 that introduces a sample, a carrier gas controller 51 (carrier gas supply section) that supplies a carrier gas, a detector 60, a make-up gas controller 82 (make-up gas supply section) that supplies a make-up gas, and a computer 20 that controls the column oven 2, the carrier gas controller 51, and the make-up gas controller 82.

The column oven 2 includes a housing 10 that has a cubic shape and is composed of four walls 12 on the top, bottom, left, and right sides, a back wall 16, and a front door 15 as a front wall. The housing 10 includes therein a column 11 for a sample gas to pass through, a radial fan 14 for circulating air, and a heater 13 for heating the air. The front door 15 is adapted to be opened/closed with a left end thereof as a shaft. The analyst may open the front door 15 to replace the column 11 inside the housing 10 with other columns. Moreover, an exhaust opening (not shown) is formed on the top of the back wall 16, and an exhaust door, adapted to be opened/closed, is disposed on the exhaust opening. By opening the exhaust door, the air inside the housing 10 may be exhausted outside via the exhaust opening. Furthermore, an intake opening 33 is formed at a center of the back wall 16, and an intake door 37, also adapted to be opened/closed, is disposed on the intake opening 33. Air may be introduced into the housing 10 from the outside via the intake opening 33 by opening the intake door 37.

Descriptions of the sample vaporization chamber 70 and the carrier gas controller 51 are provided below. FIG. 6 is an enlarged cross-sectional view of the sample vaporization chamber 70 and the carrier gas controller 51. The sample vaporization chamber 70 includes an enclosure 71 made of a metal and having a cylindrical shape and a heater 78 heating an outer surface of the enclosure 71. The enclosure 71 may be divided into a top enclosure 71b and a bottom enclosure 71a, so as to dispose a glass insert 77a made of glass and having a cylindrical shape into the enclosure 71.

The top enclosure 71b has a sample intake opening 72 on a top side thereof for introducing a sample S. The bottom enclosure 71a has a carrier gas intake opening 73 on a left wall thereof for introducing the carrier gas, a purge opening 74 on a right wall thereof for exhausting the carrier gas, a column connection opening 75 formed on a bottom side to be connected with the inlet end of the column 11, and a split opening 76 on the right wall for exhausting a portion of the sample gas introduced into the enclosure 71 with the carrier gas.

A column-shaped septum 72a made of silicone rubber is disposed on the sample intake opening 72. The septum 72a is pressed down by a septum nut 72b and fixed to the top enclosure 71b. When performing an analysis, the analyst may insert a needle 91 of a microsyringe 90 that contains the sample S into the septum 72a to drip the sample S into the enclosure 71. Because the septum 72a is elastic, the septum 72a forms a hole when the needle 91 is inserted and the hole is blocked as soon as the needle 91 is removed.

The glass insert 77a is supported by a circular seal ring 77b inside the bottom enclosure 71a. When performing the analysis, the analyst may place the needle 91 of the microsyringe 90 at the top of an inner space formed inside the glass insert 77a and drip the sample S through the inner space of the glass insert 77a from the top to the bottom to vaporize the sample S.

The top enclosure 71b is pressed down by a seal nut 77c and fixed to the bottom enclosure 71a. Moreover, the column connection opening 75 is connected with the inlet end of the column 11 and fixed by a column nut 75a.

The carrier gas is enclosed in a gas supply source 52. The gas supply source 52 is connected with an end of a gas intake tube. The other end of the gas intake tube is connected with the carrier gas intake opening 73 through a flow meter 51a and a control valve 51b. The flow meter 51a is used for measuring a flow $H_1$ of the carrier gas at a set time interval. Based on this configuration, the control valve 51b is controlled while the flow $H_1$ of the carrier gas is measured by the flow meter 51a at the set time interval, thereby adjusting the flow $H_1$ of the carrier gas supplied to the carrier gas intake opening 73.

An end of a gas exhaust tube is connected with the split opening 76, and a control valve 51f and a split vent 51g are disposed on the gas exhaust tube, so as to exhaust a certain ratio of the carrier gas, i.e. flow $H_4$, via the split opening 76 when the control valve 51f is opened. An end of a gas exhaust tube is connected with the purge opening 74. Moreover, a pressure meter 51c for detecting a pressure inside the enclosure 71, a control valve 51d, and a purge vent 51e are disposed on the gas exhaust tube, so as to exhaust a certain ratio of the carrier gas, i.e. flow $H_3$, via the purge opening 74 when the control valve 51d is opened.

The detector 60 is a flame ionization detector (FID), flame photometric detector (FPD), thermal conductivity detector (TCD), etc., for example, used for burning and releasing the make-up gas of a flow $H_5$. The make-up gas is enclosed in a gas supply source 81. An end of a gas intake tube is connected with the gas supply source 81, and the other end of the gas intake tube is connected with the detector 60 through a control valve 82a, a pressure sensor 82b, and a resistance pipe 82c. The pressure sensor 82b is used for measuring the pressure inside the gas intake tube at a set time interval. With this configuration, the control valve 82a is controlled while a flow $H_2$ of the make-up gas is measured by the pressure sensor 82b and the resistance pipe 82c at the set time interval, thereby adjusting the flow $H_2$ of the make-up gas supplied to the detector 60.

The computer 20 includes a CPU 21 (controller) and a memory 22 (memory section), etc., and an input device 23 having a keyboard and a mouse, etc., and a display device 24 are connected thereto. In terms of the functions performed by the CPU 21 as illustrated by a block diagram, the CPU 21 includes a temperature controlling section 21a that controls the heater 31, etc., a flow controlling section 21c that controls the carrier gas controller 51 and the make-up gas controller 82, an analysis controlling section 21d that receives a signal from the detector 60, and a monitoring section 21b that monitors the hydrogen gas concentration.

In the gas chromatography device 101, the temperature and time for performing the analysis are inputted via the input device 23, and the temperature controlling section 21 a supplies power to the heater 13 to heat the air and supplies power to a motor to turn on the radial fan 14 for circulating the heated air, so as to make the temperature in the housing 10 uniform for analysis. If the temperature in the housing 10 is lower than the temperature required for analysis, the temperature controlling section 21a closes the exhaust door and the intake door 37 and increases the power to the heater 13 to heat the air. On the contrary, if the temperature in the housing 10 is higher than the temperature required for analysis, the power supplied to the heater 13 is reduced and the exhaust door and the intake door 37 are opened to introduce the air at room temperature into the housing 10 via the intake opening 33 and at the same time exhaust a portion of the heated air outside via the exhaust opening.

Helium is often used as the carrier gas enclosed in the gas supply source 52 and the make-up gas enclosed in the gas supply source 81. The reason is that helium is stable or is superior to other gases such as nitrogen and argon in terms of the properties of column 11 (known as theoretical plate), i.e. distribution efficiency. However, due to the concern of resource exhaustion, the price of helium gas is increasing. Hydrogen gas is as good as helium in theoretical plate. In consideration of the running cost of the analysis, it is desirable to use hydrogen gas as the carrier gas and the make-up gas.

The gas chromatography device 101 requires frequent maintenance, such as replacement of the septum 72a and the glass insert 77a of the sample vaporization chamber 70 and the column 11 of the column oven 2. After replacement, junctures between the septum 72a, the glass insert 77a, and the column 11, etc., may become slack and cannot be sealed up, and the carrier gas may leak from the housing 10 via the junctures of the septum 72a, the glass insert 77a, and the column 11. In the case of using hydrogen gas as the carrier gas, there is a high explosion risk if the concentration of the hydrogen gas in the high-temperature housing 10 is over the flammability concentration limit. For this reason, using hydrogen gas has been avoided. The flammability concentration limit of hydrogen gas is about 4%.

Therefore, a gas chromatography device (e.g. Japan Laid open publication H5-346424) has been disclosed for dealing with the leakage of hydrogen gas when hydrogen gas is used as the carrier gas. Such a gas chromatography device 101 uses a hydrogen gas detecting sensor 40 to detect the hydrogen contained in the gas collected from the housing 10 and stops an hydrogen generating device from supplying the hydrogen gas which is used as the carrier gas when the leakage of the hydrogen gas is detected.

The heat resistance of the hydrogen gas detecting sensor 40 is as low as 260° C., but the temperature in the housing 10 is about 450° C. Thus, the gas needs to be cooled in long metallic pipes (for example, 30 cm long) installed to connect with the inside of the housing 10 before being supplied to the hydrogen gas detecting sensor 40. Moreover, the air pump 142, etc., needs to be connected to the pipes for supplying the gas from the long pipes to the hydrogen gas detecting sensor 40.

SUMMARY OF THE INVENTION

Problem to be solved by the Invention

Nevertheless, the gas chromatography device 101 as described above cannot accurately detect the hydrogen gas when the piping has a hole or the air pump 142 breaks down.

Solution to the Problem

In view of the above, the inventors of the invention conceive a way to detect leakage of hydrogen gas without using the air pump 142 and long piping. Because hydrogen has a small molecule size, there are some materials that are penetrable to hydrogen gas and not to other gases. It is found that this kind of material may be disposed in the through hole formed in the housing 10. Accordingly, the heat transmitted to the hydrogen gas detecting sensor 40 can be reduced by convection of the gas from inside the housing 10 to the outside.

Accordingly, a gas chromatography device of the invention includes a column oven having a housing, a column disposed in the housing, and a heater heating air in the housing; a sample vaporization chamber supplying a sample to an inlet end of the column; a carrier gas supply section supplying a carrier gas to the sample vaporization chamber; a detector connected to an outlet end of the column; a controller controlling the heater and the carrier gas supply section; and a hydrogen gas detecting sensor detecting hydrogen gas. The carrier gas is hydrogen gas. A through hole is formed in the housing and a material that allows hydrogen to pass through but does not transmit heat is disposed in the through hole. In addition, the hydrogen gas detecting sensor is disposed near the through hole outside the housing.

The aforementioned "disposed near the through hole" means that a gap, which allows gas to be exhausted from the hydrogen gas detecting sensor, is maintained between the hydrogen gas detecting sensor and the housing. The gap is within 1 mm from the through hole, for example.

Effect of the Invention

According to the above, the gas chromatography device of the invention is adapted for detecting leakage of hydrogen gas without using an air pump and long piping.

(Solution to Other Problems and Effect thereof) Moreover, according to the invention, the material may be disposed from a center of the through hole to an exterior of the through hole. The gas chromatography device of the invention effectively guides the gas in the housing to the through hole.

In addition, according to the invention, the hydrogen gas detecting sensor is disposed with a connection tube located between the hydrogen gas detecting sensor and the through hole, and the connection tube tapers from the through hole and the cross-sectional area thereof gradually decreases. The gas chromatography device of the invention efficiently supplies gas to the hydrogen gas detecting sensor and further lowers the temperature of the gas supplied to the hydrogen gas detecting sensor.

According to the invention, the material may be glass wool, glass cloth, or a glass mat made of a glass fiber. Furthermore, according to the invention, the controller may cease supplying power to the heater and cease supplying the hydrogen gas to the sample vaporization chamber, or cease supplying power to the heater or cease supplying the hydrogen gas to the sample vaporization chamber when the hydrogen gas detecting sensor detects the hydrogen gas. When the housing containing hydrogen gas therein is determined, the gas chromatography device of the invention for example instantly ceases supplying power to the heater and ceases supplying the hydrogen gas. Since the temperature inside the column oven is lowered and the hydrogen gas in the housing is exhausted outside, fire hazards are prevented.

DESCRIPTION OF THE EMBODIMENTS

The following paragraphs explain exemplary embodiments of the invention with reference to the figures. Needless to say, the invention is not restricted to the disclosed exemplary embodiments, and various modifications may be made to the disclosure without departing from the spirit and scope of the invention.

Figure 1:
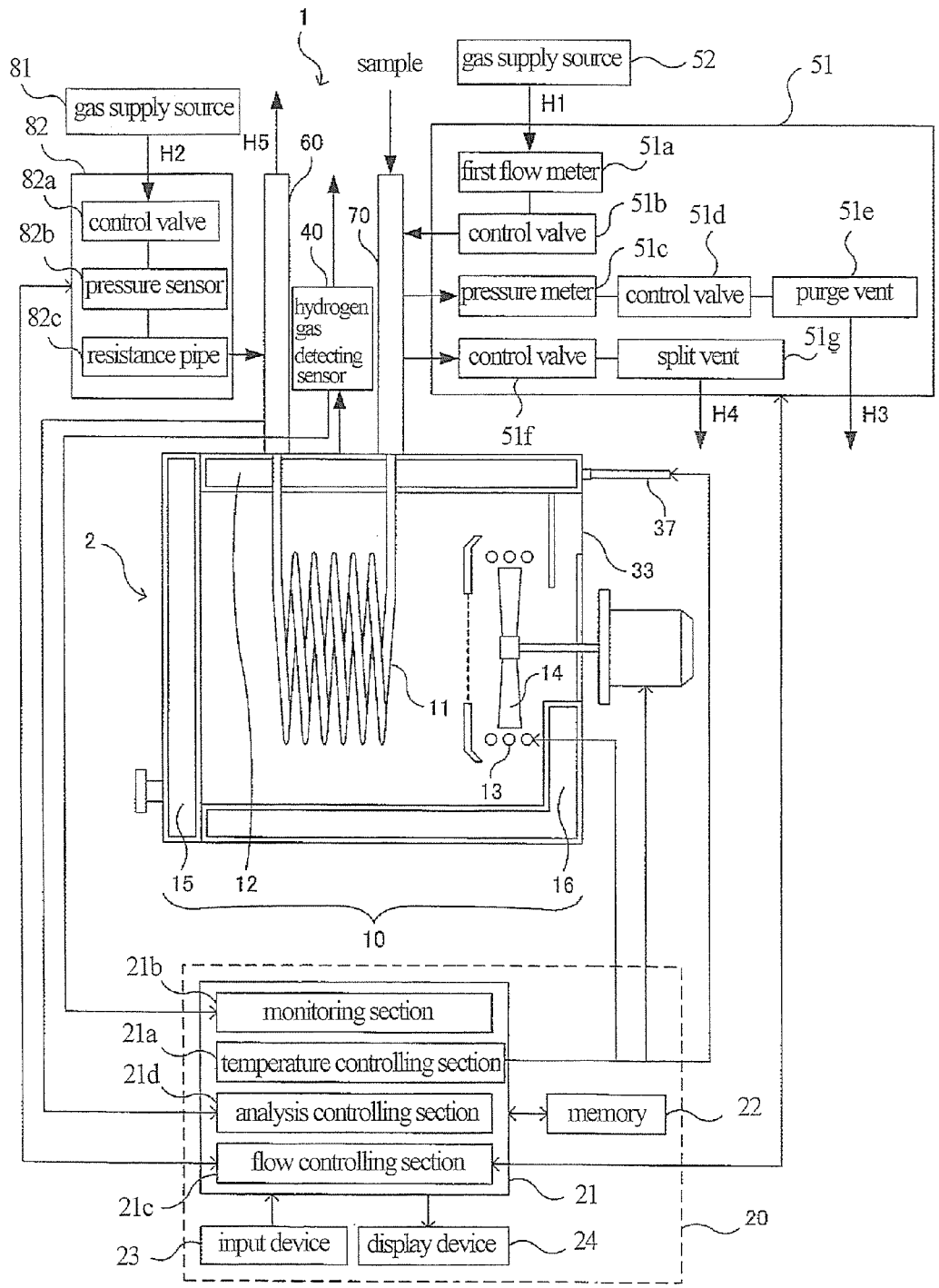
FIG. 1 is a structural diagram illustrating an example of a gas chromatography device according to the invention.
Figure 2:
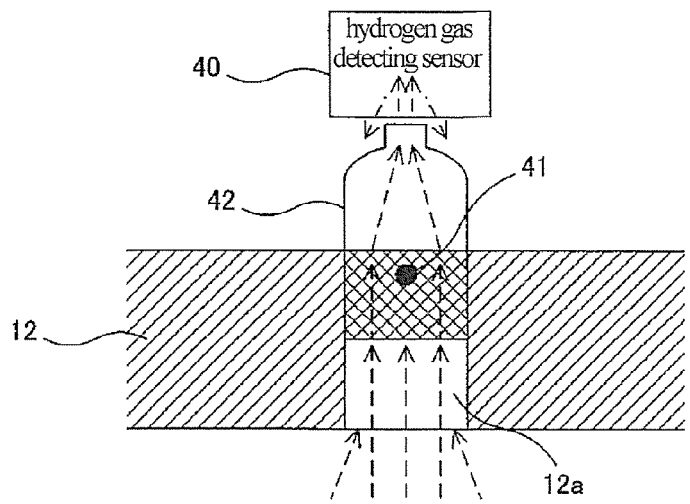
FIG. 2 is a schematic view of a hydrogen gas detecting sensor disposed above a column oven.

FIG. 1 is a structural diagram illustrating an example of a gas chromatography device according to the invention. FIG. 2 is a schematic view of a hydrogen gas detecting sensor disposed above a column oven. Elements that are the same as those of the gas chromatography device 101 are denoted by identical reference numerals. A gas chromatography device 1 includes a column oven 2; a sample vaporization chamber 70 introducing a sample; a carrier gas controller 51 (a carrier gas supply section) supplying a carrier gas; a detector 60; a make-up gas controller 82 (a make-up gas supply section) supplying a make-up gas; a computer 20 controlling the column oven 2, the carrier gas controller 51, and the make-up gas controller 82; and a hydrogen gas detecting sensor 40 detecting hydrogen gas. In addition, the hydrogen gas is enclosed in gas supply sources 52 and 81 of the invention.

The column oven 2 includes a housing 10. The housing 10 has a cubic shape and includes walls 12 covering four sides, i.e. top, bottom, left, and right sides, of the housing 10, a back wall 16, and a front door 15 as a front wall. The housing 10 further includes therein a column 11 through which a sample gas passes, a radial fan 14 circulating air, and a heater 13 that heats air. A through hole 12a having a caliber of 15 mm, for example, is formed to pass through the top wall 12 in a vertical direction, and glass wool 41 made of a glass fiber is disposed in the through hole 12a from a center thereof to an exterior, so as to ensure that the gas inside the housing 10 is guided to the through hole 12a. The glass wool 41 allows hydrogen to pass through but does not transmit heat.

The hydrogen gas detecting sensor 40 is used to detect a hydrogen gas concentration of the gas inside the housing 10. In addition, the hydrogen gas detecting sensor 40 is disposed above a connection tube 42 made of a metal and connected on the through hole 12a. The connection tube 42 is 15 mm high, for example, and gradually tapers from a circular cross-section of 15 mm in diameter (i.e. cross-section of the through hole 12a) to a circular cross-section of 6 mm in diameter. Because the hydrogen gas detecting sensor 40 is disposed on top of an interior space of the housing 10, the hydrogen gas that has a specific gravity less than that of air is effectively detected. Preferably, the area of an outlet cross-section of the connection tube 42 is less than 70% of the area of an inlet cross-section of the connection tube 42, so as to efficiently supply gas to the hydrogen gas detecting sensor 40 and further lower the temperature of the gas supplied to the hydrogen gas detecting sensor 40.

The computer 20 includes a CPU 21 (controller) and a memory 22, and an input device 23, which has a keyboard and a mouse, etc., and a display device 24 are connected thereto. Moreover, in terms of the functions performed by the CPU 21 as illustrated by a block diagram, the CPU 21 includes a temperature controlling section 21a that controls the heater 31, etc., a flow controlling section 21c that controls the carrier gas controller 51 and the make-up gas controller 82, an analysis controlling section 21d that receives a signal from the detector 60, and a monitoring section 21b that monitors the hydrogen gas concentration according to a detection signal of the hydrogen gas detecting sensor 40.

The monitoring section 21b monitors the hydrogen gas concentration according to the detection signal of the hydrogen gas detecting sensor 40 at all times or during a period of time when control valves 51b and 82a are opened, so as to determine for example whether the hydrogen gas concentration is over 1% after the safety factor and detection error, etc. are taken into consideration, based on the detection signal of the hydrogen gas detecting sensor 40. If it is determined that the hydrogen gas concentration is over 1%, an exhaust door is opened via the temperature controlling section 21a to promptly exhaust the hydrogen gas that fills the housing 10 to the outside. Moreover, the power supplied from the temperature controlling section 21a to the heater 13 is stopped to lower the temperature inside the housing 10 and prevent causing fire. Furthermore, the control valves 51b and 82a are closed, and the supply of the hydrogen gas to the sample vaporization chamber 70 and the detector 60 is ceased. In order to facilitate the exhaust of the hydrogen gas remaining in the housing 10, a rotary speed of the radial fan 14 may be raised to increase air flow.

According to the above, the gas chromatography device 1 is adapted for detecting leakage of hydrogen gas without using an air pump or long piping.

Figure 3:
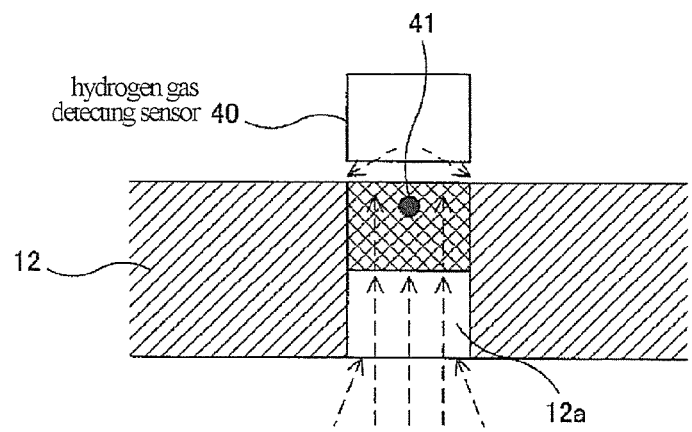
FIG. 3 is a schematic view illustrating another example of the hydrogen gas detecting sensor disposed above the column oven.
Figure 4:
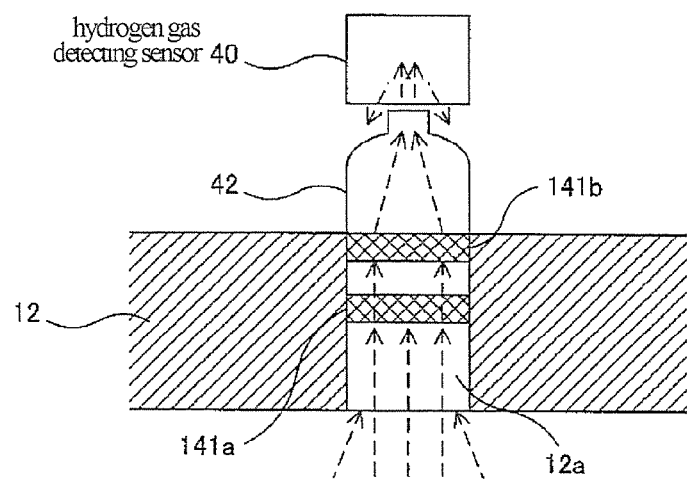
FIG. 4 is a schematic view illustrating yet another example of the hydrogen gas detecting sensor disposed above the column oven.
Figure 5:
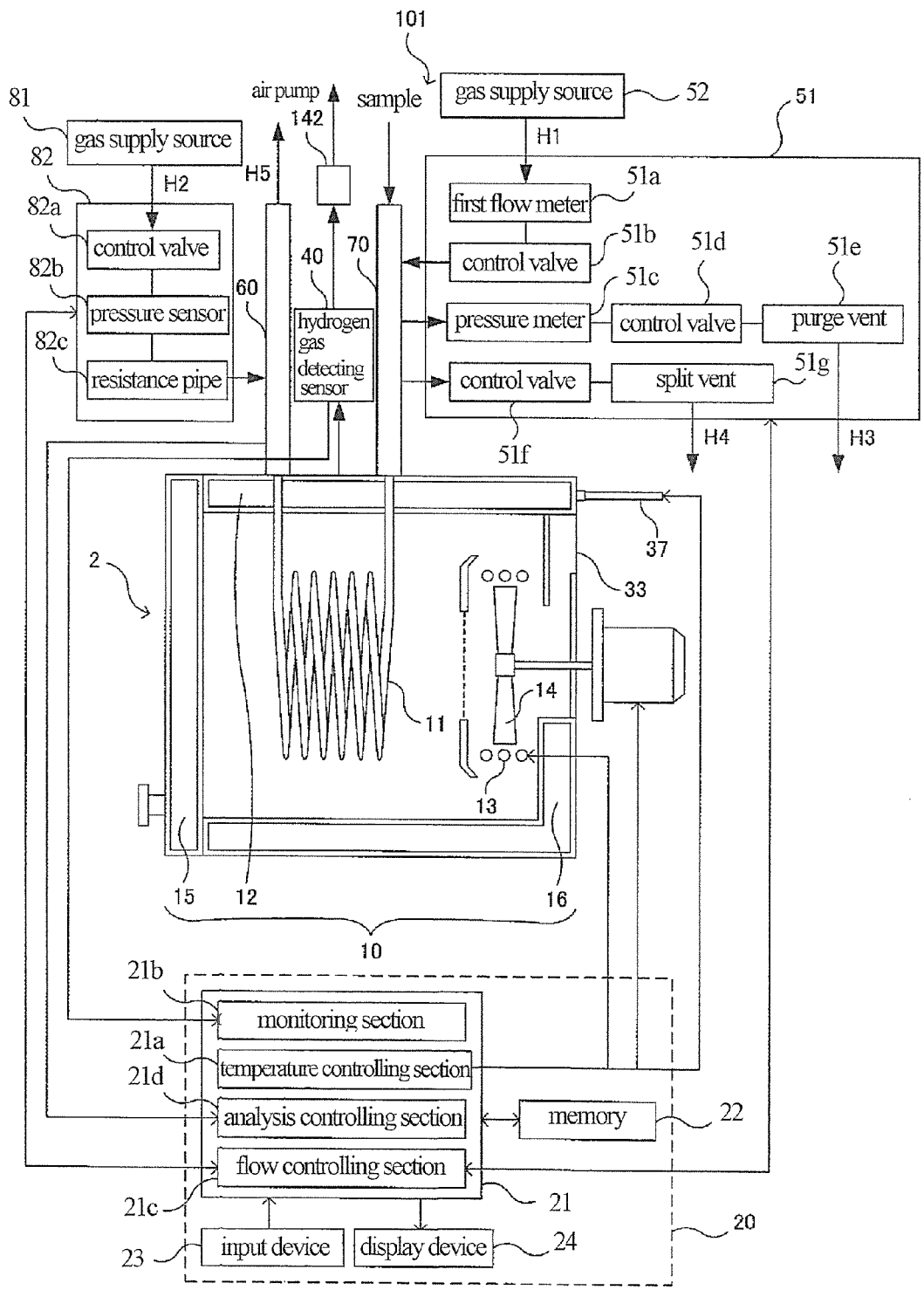
FIG. 5 is a structural diagram illustrating an example of the conventional gas chromatography device.
Figure 6:
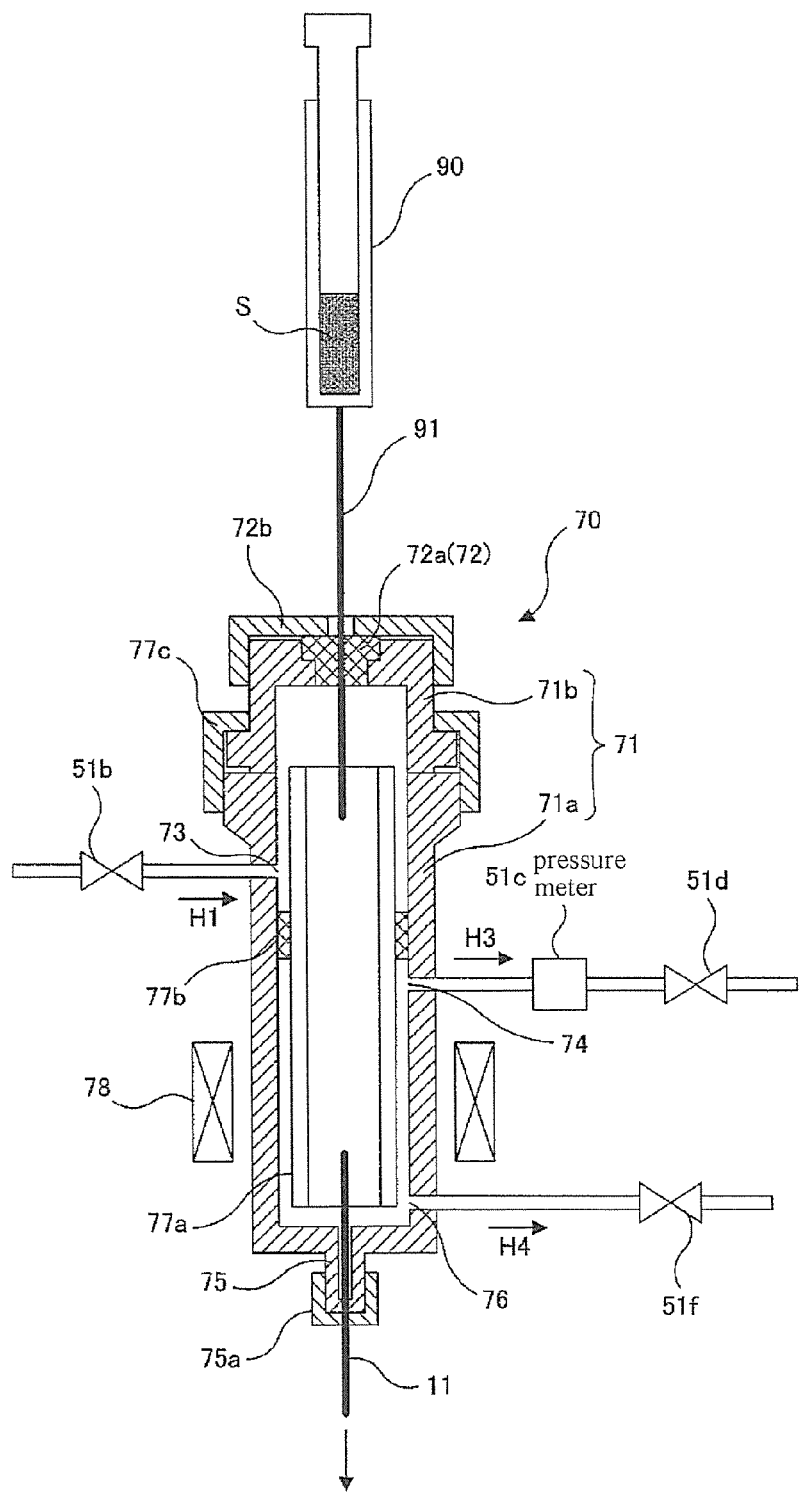
FIG. 6 is an enlarged cross-sectional view illustrating a sample vaporization chamber and a carrier gas controller.

OTHER EMBODIMENTS (1) According to the above disclosure, the hydrogen gas detecting sensor 40 of the gas chromatography device 1 is disposed with the connection tube 42 located between the hydrogen gas detecting sensor 40 and the through hole 12a, and the connection tube 42 tapers from the through hole 12a and the cross-section area thereof gradually decreases. However, the hydrogen gas detecting sensor 40 may be disposed without the connection tube between the hydrogen gas detecting sensor 40 and the through hole 12a (as shown in FIG. 3).

(2) According to the above disclosure of the gas chromatography device 1, the glass wool 41 is disposed from the center of the through hole 12a to the exterior. However, a thinner glass wool 141a may be disposed at the center of the through hole 12a and a thinner glass wool 141b may be disposed in the through hole 12a near the exterior.

INDUSTRIAL APPLICABILITY

The invention is adapted for a gas chromatography device.

What is claimed is:

1. A gas chromatography device, comprising:
   a column oven, comprising a housing, a column disposed in the housing, and a heater heating air in the housing;
   a sample vaporization chamber supplying a sample to an inlet end of the column;
   a carrier gas supply section supplying a carrier gas to the sample vaporization chamber;
   a detector connected to an outlet end of the column;
   a controller controlling the heater and the carrier gas supply section; and
   a hydrogen gas detecting sensor detecting hydrogen gas, wherein the carrier gas is the hydrogen gas,
   wherein a through hole is formed in the housing, a material is disposed in the through hole, and the material is an insulating material that allows hydrogen to pass through, and
   wherein the hydrogen gas detecting sensor is disposed above the through hole outside the housing with a gap between the hydrogen gas detecting sensor and the housing, wherein the gap allows gas to be exhausted from the hydrogen gas detecting sensor.

2. The gas chromatography device according to claim 1, wherein the material is disposed from a center of the through hole to an exterior of the through hole.

3. The gas chromatography device according to claim 1, wherein the hydrogen gas detecting sensor is disposed with a connection tube located between the hydrogen gas detecting sensor and the through hole, and the connection tube tapers from the through hole and a cross-section area of the connection tube gradually decreases.

4. The gas chromatography device according to claim 1, wherein the material is glass wool, glass cloth, or a glass mat made of a glass fiber.

5. The gas chromatography device according to claim 1, wherein the controller ceases supplying power to the heater and ceases supplying the hydrogen gas to the sample vaporization chamber, or cease supplying power to the heater or cease supplying the hydrogen gas to the sample vaporization chamber when the hydrogen gas detecting sensor detects the hydrogen gas.

* * * * *